(12) United States Patent
Dijcks et al.

(10) Patent No.: US 8,367,648 B2
(45) Date of Patent: Feb. 5, 2013

(54) SUBSTITUTED 16,17-ANNELLATED STEROID COMPOUNDS FOR USE IN WOMENS HEALTHCARE

(75) Inventors: Fredericus Antonius Dijcks, Oss (NL); Hubert Jan Jozef Loozen, Oss (NL); Samira Addo, Oss (NL); Antonius Gerardus Hendrikus Ederveen, Oss (NL)

(73) Assignee: MSD OSS B.V., Oss (NL)

( * ) Notice: Subject to any disclaimer, the term of this patent is extended or adjusted under 35 U.S.C. 154(b) by 290 days.

(21) Appl. No.: 12/795,970

(22) Filed: Jun. 8, 2010

(65) Prior Publication Data

US 2010/0331292 A1    Dec. 30, 2010

Related U.S. Application Data

(60) Provisional application No. 61/185,801, filed on Jun. 10, 2009.

(51) Int. Cl.
*A61K 31/56* (2006.01)
*C07J 53/00* (2006.01)

(52) U.S. Cl. ...................................... 514/182; 552/514
(58) Field of Classification Search ................... 552/514; 514/182
See application file for complete search history.

(56) References Cited

U.S. PATENT DOCUMENTS
2002/0156271 A1    10/2002    Muller et al.

FOREIGN PATENT DOCUMENTS

| EP | 0 869 132 B1 | 9/2001 |
|---|---|---|
| EP | 1 550 447 A1 | 7/2005 |
| WO | 02/00682 A1 | 1/2002 |

*Primary Examiner* — Barbara P Badio
(74) *Attorney, Agent, or Firm* — Kenrick L. Vidale; Janet E. Fair; John C. Todaro

(57) ABSTRACT

The present invention relates to substituted steroid compounds having the formula

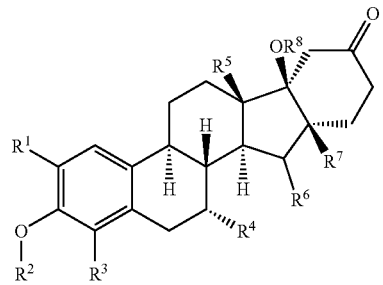

Wherein $R^1$ is H or halogen; $R^2$ is H, (1C-4C)alkyl, (1C-4C) acyl, glucuronyl or sulfamoyl; $R^3$ is H or halogen; $R^4$ is H, (1C-4C)alkyl, (2C-4C)alkenyl or (2C-4C)alkynyl; $R^5$ is methyl or ethyl; $R^6$ is H or methyl; $R^7$ is H or methyl; $R^8$ is H or acyl for use in the treatment and prevention of endometriosis, for contraception, for hormonal therapy in perimenopausal and post-menopausal women, for the treatment of osteoporosis and for the treatment uterine fibroids and other menstrual-related disorders, such as dysfunctional uterine bleeding.

18 Claims, 1 Drawing Sheet

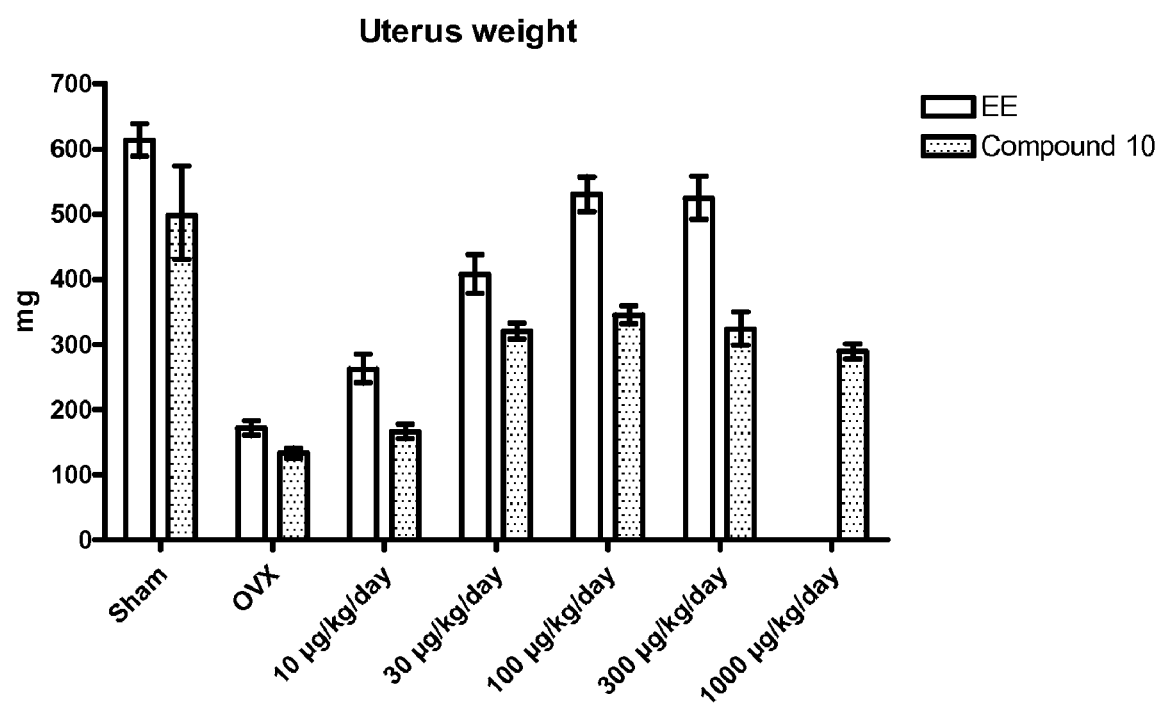

SUBSTITUTED 16,17-ANNELLATED STEROID COMPOUNDS FOR USE IN WOMENS HEALTHCARE

FIELD OF THE INVENTION

The present invention relates to steroid compounds having a 16,17-annellated carbocyclic ring, and relates to new means for the treatment and prevention of endometriosis, for contraception, for hormonal therapy in perimenopausal and postmenopausal women, for the treatment of osteoporosis and for the treatment uterine fibroids and other menstrual-related disorders, such as dysfunctional uterine bleeding.

BACKGROUND OF THE INVENTION

Steroid compounds having a 16,17-annellated carbocyclic ring for use in therapeutic methods based on estrogen receptor (ER) activation, in particular selective activation of the ERα (ERalpha), are disclosed in WO 2002/00682 and EP869132. Such compounds are intended for use as contraceptives or anti-osteoporosis agents. For therapeutic compounds in this field it is very important to provide safe treatment with a minimum of side effects, in particular on the endometrium and with regard to breast tenderness, weight gain, mood and acne.

Preventing, reversing endometriosis is an important goal in the field of women's health care. Endometriosis is a painful gynecological condition that is characterized by the presence of endometrial tissue in sites outside of the uterine cavity. The prevalence rate is approximately 10% but this may be an underestimate because of the need to perform a laparoscopic procedure to determine the presence of disease. The disease affects women of reproductive age, the most common symptoms being painful menstruation (dysmenorrhoea), pain during intercourse (dyspareunia), painful bowel movement (dyschezia), chronic pelvic pain, heavy periods (menorrhagia), and infertility. If left untreated or inadequately treated endometriosis can either progress or spontaneously regress. In a significant number of women endometriosis is a chronic progressive disease manifesting itself as intractable pain, worsening quality of life, and infertility.

The etiology is unclear which also hampers an understanding of the symptomatic implications of the disease. Endometriosis produces an array of symptoms of varying severity with lack of correlation between stage of disease, disease load and degree of pain thereby causing confusion with clinical classification and delay in diagnosis. Known treatment options are drug therapy and conservative surgery.

Drug therapy is with analgesics, hormonal contraceptives which contain both estrogen and progestagen (Combined Oral Contraceptive (COC)) or progestagen only (Progestagen-Only Contraceptive (POC)), gonadotropin releasing hormone (GnRH) agonists, or other hormones e.g. danazol. Oral contraceptive regimes with combined use of an estrogen and a progestagen (COC) are widely used as first-line therapy in suspected or diagnosed endometriosis, owing to their property to provide cycle control, reduce menstrual flow and eradicate dysmenorrhoea, the most common symptom especially in early-stage disease. However, no single product offers sufficient efficacy in combination with a tolerable level of side effects. COCs may treat some of the symptoms well, but do not effectively suppress the progress of endometriosis and do not effectively treat chronic pelvic pain.

COCs produce initial decidualization of the endometrium by creating a state of pseudocyesis and later atrophy and thinning of the endometrium, thereby providing cycle control, reduction in menstrual flow and reduction of dysmenorrhoea. COCs may treat therefore menstruation-related symptoms but they do not completely suppress the growth of endometriotic lesions and associated chronic pelvic pain.

The mechanism of action of progestagens is initial decidualization of endometrium, followed by atrophy as a result of a direct suppressive effect on estrogen receptors in the endometrium. There is evidence that progestagens suppress matrix metalloproteinases at the molecular level thereby inhibiting the growth of ectopic endometrium. Medroxyprogesterone acetate is the most widely used progestagen for the treatment of endometriosis. Although available for oral administration, medroxyprogesterone acetate is usually administered as a depot formulation every 3 months. The side effects of POCs are multiple, the commonest being breakthrough bleeding, nausea, fluid retention and breast tenderness.

GnRH agonists down-regulate the Hypothalamus-Pituitary-Ovary axis resulting in a hypo-estrogenic menopausal state, endometrial atrophy, and amenorrhoea. Multiple side effects related to menopausal symptoms as well as osteoporosis limit duration of treatment to 6 months.

Known drug treatments and/or conservative surgery offer temporary relief only and relapse rates can be as high as 50% with a major impact on fertility and quality of life. Moreover, a significant number of women aged 40-44 years require hysterectomy and bilateral salpingo-oophorectomy.

There is a strong need for early therapeutic intervention that improves on the above-mentioned shortcomings of available treatment options. The need is in particular for early therapeutic intervention that suppresses progression of disease and/or improves the side-effect profile (i.e. unscheduled bleeding) and improves fertility outcomes.

SUMMARY OF THE INVENTION

It has now been found that a compound having the Formula I

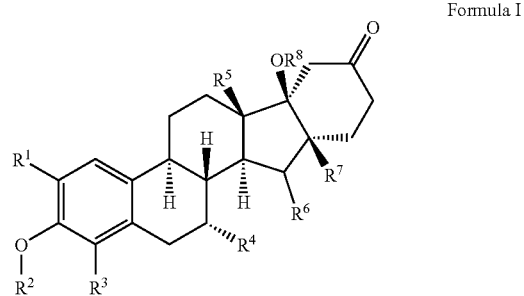

Formula I wherein $R^1$ is H or halogen; $R^2$ is H, (1C-4C)alkyl, (1C-4C)acyl, glucuronyl or sulfamoyl; $R^3$ is H or halogen; $R^4$ is H, (1-4C)alkyl, (2C-4C)alkenyl or (2C-4C)alkynyl; $R^5$ is methyl or ethyl; $R^6$ is H or methyl; $R^7$ is H or methyl and $R^8$ is H or acyl, has a particularly favourable combination of biological activities for use in medical treatments in this field, such as for preventing, reversing endometriosis as contraceptives or anti-osteoporosis agents.

BRIEF DESCRIPTION OF THE DRAWING

FIG. 1 Effect of daily oral dosing for 4 weeks with EE and Compound 10 on uterine weight of ovariectomized female rats.

DETAILED DESCRIPTION OF THE INVENTION

A compound according to the invention strikes an improved balance between safe treatment with a minimum of side effects, in particular on the endometrium and with regard to osteoporosis, breast tenderness, weight gain and/or fluid retention, mood and acne, breakthrough bleeding and nausea. A compound according to the invention can be used in the treatment of endometriosis, whereby the compound can reduce the most common symptoms of endometriosis, such as painful menstruation (dysmenorrhoea), pain during intercourse (dyspareunia), painful bowel movement (dyschezia), chronic pelvic pain, non-menstrual pelvic pain, pelvic tenderness and induration, heavy periods (menorrhagia), and infertility with important beneficial consequences for the quality of life of affected women.

The terms used in this specification are clarified as follows:

The prefixes (1C-4C) etc. have the meaning to restrict the meaning of the indicated group to those with 1 to 4 etc. carbon atoms;

The term (1C-4C) alkyl represents a branched or unbranched alkyl group having 1-4 carbon atoms. Examples of (1C-4C) alkyl groups include methyl, ethyl, propyl, isopropyl, butyl, and tertiary butyl.

The term (2C-4C) alkenyl represents a branched or unbranched alkenyl group having 2-4 carbon atoms. Examples of (2C-4C) alkenyl groups include ethenyl, 1-propenyl, and 2-propenyl.

The term (1C-4C) alkynyl represents an alkynyl group having 2-4 carbon atoms. Examples of (2C-4C) alkynyl groups include ethynyl and 1-propynyl.

The term (1C-4C) acyl and acyl without further specifying prefix represent an acyl group derived from a carboxylic acid having respectively 1-4 or, respectively, an unspecified number of carbon atoms. The (1C-4C) acyl group can comprise a hydrocarbon which may be branched, unbranched, saturated or unsaturated. Examples of (1C-4C) acyl groups include formyl, acetyl, propanoyl, propenyl and pivaloyl. When acyl is not specified in size it indicates that it is less critical how the acyl group is defined. It may not only be in the short range of, e.g. 1C-6C carbon atoms, but can also mean a long chained acyl group for example of size having 6C-34C carbon atoms or 8C-24C or any group of smaller range or with less sizeable aliphatic moiety, examples of which are 8C-20C or 10C-16C, which include decanoyl and undecanoyl. Such more sizeable (1C-34C) or (1C-24C)acyls, optionally further substituted, are very suitable to use as prodrugs for extended release of the active unesterified compound. Ester prodrugs can be made by esterification of each or both of the two hydroxyl groups in the general formula 1. Other prodrugs can be with a sugar moiety to the 3 hydroxyl group, for example the glucuronide to the 3-hydroxy group of the compound according to the invention.

This invention can be realized in a number of embodiments:

It is one such more specific embodiment wherein $R^1$, $R^2$, $R^3$, $R^4$, $R^5$, $R^6$ and $R^7$ are as defined above and $R^8$ is H.

In two other embodiments the compound is as in the main definition of the invention or as in the more specific embodiment described above whereby in each $R^1$ is H or F and $R^3$ is H or F.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl or ethyl; $R^6$ is H or α-methyl; $R^7$ is H or methyl and $R^8$ is H or acyl.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl or ethyl; $R^6$ is H or α-methyl; $R^7$ is H or methyl and $R^8$ is H.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl; $R^6$ is H or methyl; $R^7$ is H or methyl and $R^8$ is H or acyl.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl; $R^6$ is H or methyl; $R^7$ is H or methyl and $R^8$ is H.

In another embodiment $R^1$ is H or halogen; $R^2$ is H, (1C-4C)alkyl, (1C-4C)acyl or sulfamoyl; $R^3$ is H or halogen; $R^4$ is (1C-4C)alkyl; $R^5$ is methyl or ethyl; $R^6$ is H or methyl; $R^7$ is H or methyl and $R^8$ is H or acyl.

In another embodiment $R^1$ is H or halogen; $R^2$ is H, (1C-4C)alkyl, (1C-4C)acyl or sulfamoyl; $R^3$ is H or halogen; $R^4$ is (1C-4C)alkyl; $R^5$ is methyl or ethyl; $R^6$ is H or methyl; $R^7$ is H or methyl and $R^8$ is H.

In another embodiment $R^1$ is H or halogen; $R^2$ is H, (1C-4C)alkyl, (1C-4C)acyl or sulfamoyl; $R^3$ is H or halogen; $R^4$ is propyl; $R^5$ is methyl or ethyl; $R^6$ is H or methyl; $R^7$ is H or methyl and $R^8$ is H or acyl.

In another embodiment $R^1$ is H or halogen; $R^2$ is H, (1C-4C)alkyl, (1C-4C)acyl or sulfamoyl; $R^3$ is H or halogen; $R^4$ is propyl; $R^5$ is methyl or ethyl; $R^6$ is H or methyl; $R^7$ is H or methyl and $R^8$ is H.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl; $R^6$ is H; $R^7$ is H and $R^8$ is H or acyl.

In another embodiment $R^1$ is H or halogen; $R^2$ is H, (1C-4C)alkyl, (1C-4C)acyl or sulfamoyl; $R^3$ is H or halogen; $R^4$ is H, (1-4C)alkyl, (2C-4C)alkenyl or (2C-4C)alkynyl; $R^5$ is methyl; $R^6$ is H; $R^7$ is H and $R^8$ is H.

In another embodiment $R^1$ is H or F; $R^2$ is H, (1C-4C)alkyl, (1C-4C)acyl or sulfamoyl; $R^3$ is H or F; $R^4$ is H, (1-4C)alkyl, (2C-4C)alkenyl or (2C-4C)alkynyl; $R^5$ is methyl; $R^6$ is H; $R^7$ is H and $R^8$ is H or acyl In another embodiment $R^1$ is H or F; $R^2$ is H, (1C-4C)alkyl, (1C-4C)acyl or sulfamoyl; $R^3$ is H or F; $R^4$ is H, (1-4C)alkyl, (2C-4C)alkenyl or (2C-4C)alkynyl; $R^5$ is methyl; $R^6$ is H; $R^7$ is H and $R^8$ is H.

In another embodiment $R^1$ is H or F; $R^2$ is H, (1C-4C)alkyl, (1C-4C)acyl or sulfamoyl; $R^3$ is H or F; $R^4$ is propyl; $R^5$ is methyl; $R^6$ is H; $R^7$ is H and $R^8$ is H or acyl In another embodiment $R^1$ is H or F; $R^2$ is H, (1C-4C)alkyl, (1C-4C)acyl or sulfamoyl; $R^3$ is H or F; $R^4$ is propyl; $R^5$ is methyl; $R^6$ is H; $R^7$ is H and $R^8$ is H.

In another embodiment $R^1$ is H or halogen; $R^2$ is H or (1C-4C) acyl; $R^3$ is H or halogen; $R^4$ is H, (1-4C)alkyl, (2C-4C)alkenyl or (2C-4C)alkynyl; $R^5$ is methyl or ethyl; $R^6$ is H or methyl; $R^7$ is H or methyl and $R^8$ is H or acyl.

In another embodiment $R^1$ is H; $R^2$ is H or (1C-4C) acyl; $R^3$ is H; $R^4$ is propyl; $R^5$ is methyl; $R^6$ is H; $R^7$ is H and $R^8$ is H or acyl.

In another embodiment $R^1$ is H; $R^2$ is H; $R^3$ is H; $R^4$ is propyl; $R^5$ is methyl; $R^6$ is H; $R^7$ is H and $R^8$ is H or acyl.

In a further embodiment of the invention, a compound according to the invention is used to treat endometriosis in view of an anti-proliferative effect on the endometrium and an anti-proliferative and anti-inflammatory effect on the endometriotic tissue. With the improvement in tolerability, a compound according to the present invention can also provide a simple effective treatment, preferably by the oral route of administration, in an early stage of the disease in a patient population familiar with contraceptive methods. Oral treatment is available by administration of a compound according to the invention in a pharmaceutical formulation. During treatment with a compound according to the invention, regular bleeding can be partially or completely avoided (inducing amenorrhoea). This is particularly useful in the treatment of endometriosis since it diminishes or prevents retrograde menstruation and thereby minimizes recurrence of disease.

A compound according to the invention can also be used for contraception. Furthermore, in view of the property of the compounds according to the invention to diminish or prevent regular bleeding, a compound according to the invention is also very useful for use in hormonal therapy in perimenopausal and post-menopausal women, e.g. for treatment of climacteric complaints, whereby inducing amenorrhoea is a highly desirable effect. A compound according to the invention has therapeutic and contraceptive effect while inducing a mostly atrophic or inactive endometrium with some subjects showing conversion to secretory (P-type) endometrium. This treatment thereby avoids endometrial proliferation or hyperplasia. Compounds according to the invention are also useful for treatment of other menstrual-related conditions such as fibroids and dysfunctional uterine bleeding and for treatment of osteoporosis.

Without intending to be bound by theory, it seems that the compound according to the present invention is able to counterbalance by a partial estrogenic activity the progressive decline in production of estrogens in perimenopausal and postmenopausal women thereby helping these women smoothly through the menopause. The partial anti-estrogenic activity of these compounds is believed to be responsible for the superior anti-proliferative effects on the endometrium, indicated as endometrial safety, reduced angiogenesis, and the potential to treat endometriosis both at the symptomatic and molecular level by targeting and modifying the disease by antagonizing local activation of ERα and ERβ in the endometriotic tissues (for a review see Bulun et al., N Engl J Med 2009; 360:268-79).

A most surprising finding is the property of a compound according to the invention to combine partial estrogenic activity with a partial progestagenic effect and partial anti-progestagenic effect. Both activities are observed at concentrations in the nanomolar range. The partial (anti-)estrogenic/(anti-)progestagenic profile of the compound is believed to be responsible for arrest of follicular growth and ovulation inhibition (partial progestagenic activity), endometrial safety (partial progestagenic and partial anti-estrogenic activity), an improved bleeding profile (partial anti-progestagenic and partial anti-estrogenic activity), endometriotic lesion regression (partial progestagenic and partial anti-estrogenic activity), and a better general side-effect profile (on breast tenderness, weight gain, mood, acne, etc.) as compared to known estrogenic/progestagenic combination treatment.

In view of the combined effects on estrogen and progestagen receptors in a single compound, a compound according to the invention is particularly advantageous because it can be used in the medical uses mentioned herein as active ingredient of a medicine without need of combining with treatment with a progestagenic or anti-progestagenic compound. The presence of both anti-progestagenic and progestagenic activity in a compound according to the invention provides for a medicinal effect which can be obtained with related prior art compounds only by drug combination treatment regimes as for example in COC.

The compound according to the invention has particular advantages in view of its safety in medical use.

In comparison to prior art compounds, in particular some of those disclosed in WO 2002/00682, the compound according to the invention has a much reduced estrogenic agonist activity. Rather, it is an antagonist with some remaining agonist effect on ERα, indicated herein as a partial (anti-)estrogenic effect. This reduces the disadvantage of an excessive estrogenic effect even further. Furthermore, a compound according to the invention has improved bioavailability. A smaller impact of metabolites, in comparison to some of these prior art compounds, has the advantage to reduce the chance to induce other non-therapeutic and adverse side-effects.

Treatment of endometriosis with a compound according to the invention provides an improvement in view of suppression of the growth of lesions in comparison to treatment of endometriosis with a combination of an estrogen and a progestagen. The partial progestagen receptor interaction in combination with the partial anti-estrogenic interaction profile of a compound according to the invention has anti-proliferative effects, not only on the endometrium, but also on the endometriotic lesion, thereby targeting the disease at a more primary molecular level and obtaining a more favourable treatment effect whilst safeguarding the endometrial safety profile.

A compound according to the invention contains a cyclohexanone ring annellated to the 16,17-position of the steroid skeleton. Methods for annellating rings have already been outlined e.g. in Loozen et al. (EP 0.869.132). Procedures generally make use of a properly functionalized chain at the C16α-position which via organometallic intermediates (e.g. derived from alkali or rare earth metals like samarium) are ring-closed to the C17α-position. In order to obtain the claimed products (i.e. with an additional ketone function in the annellated ring), proper functionality (like double bonds, ketals etc.) has to be in place, which allows conversion into these ketones after ring closures have been carried out. Optionally one or more additional steps have to be performed in order to remove other protecting groups (like 3-benzyl, alkyl- or silyl-ethers). More specific attachment of a ketal-protected 16α-butanone fragment is most effective to this end.

Deprotection of the ketal function and submitting the material to aldol-type conditions efficiently provides annellated cyclohexanone structures. An example of this is found in Scheme 1 (See references 6a, 6b and 6c for the synthons used).

Scheme 1

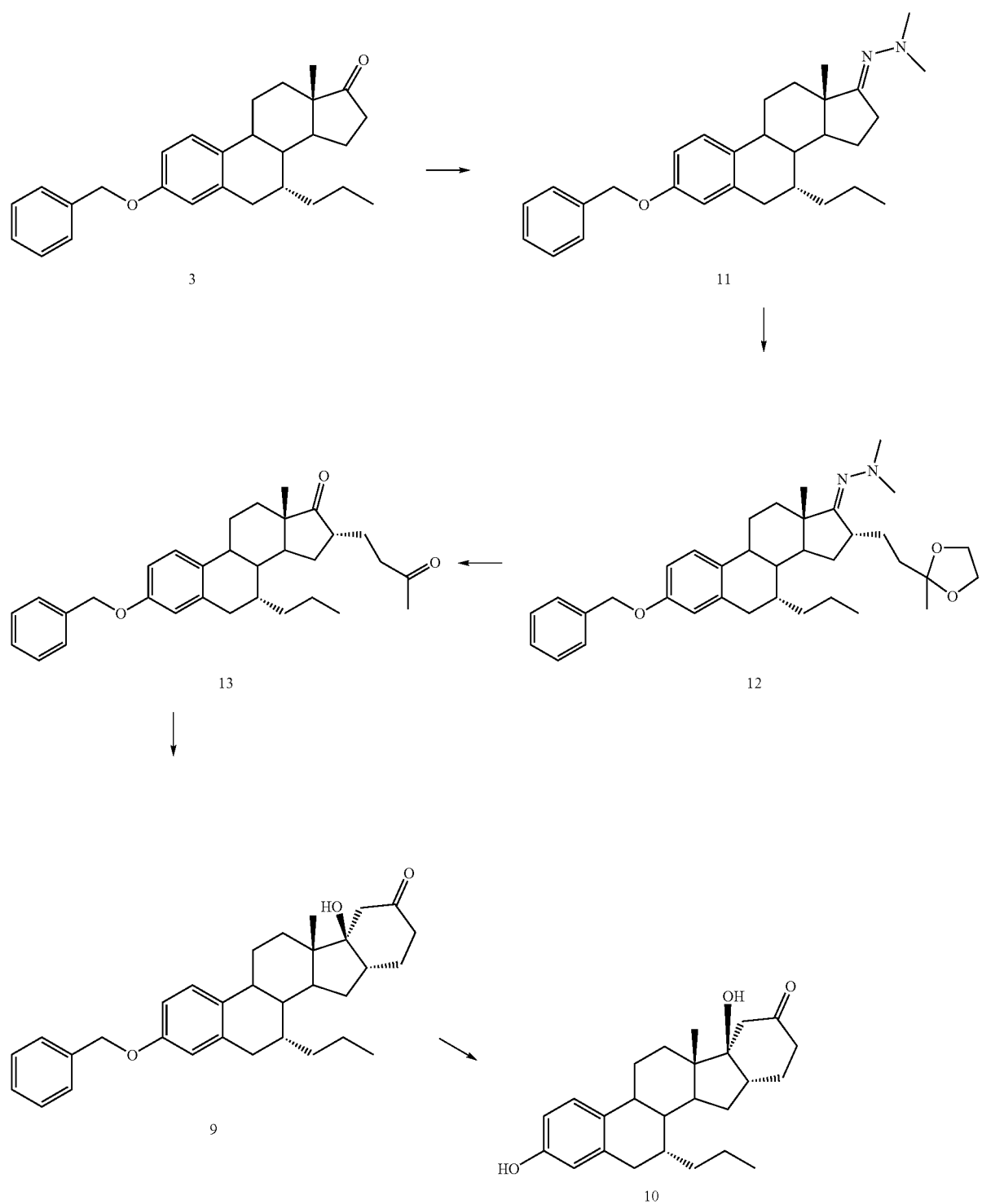

Alternatively, upon applying well-known metathesis reactions (with catalytic systems derived from Ru, Mo and W) suitably functionalized 16α,17α-olefinic chains can be converted to cyclohexenes (Reference 1). These, upon undergoing various routine functional group transformations, like epoxidation, reductive ring opening and oxidation, produce ketones as formulated.

The starting materials to that end are preferably easily available 16α,17α-diallyl steroids, such as compound 5 (see Scheme 2).
Scheme 2
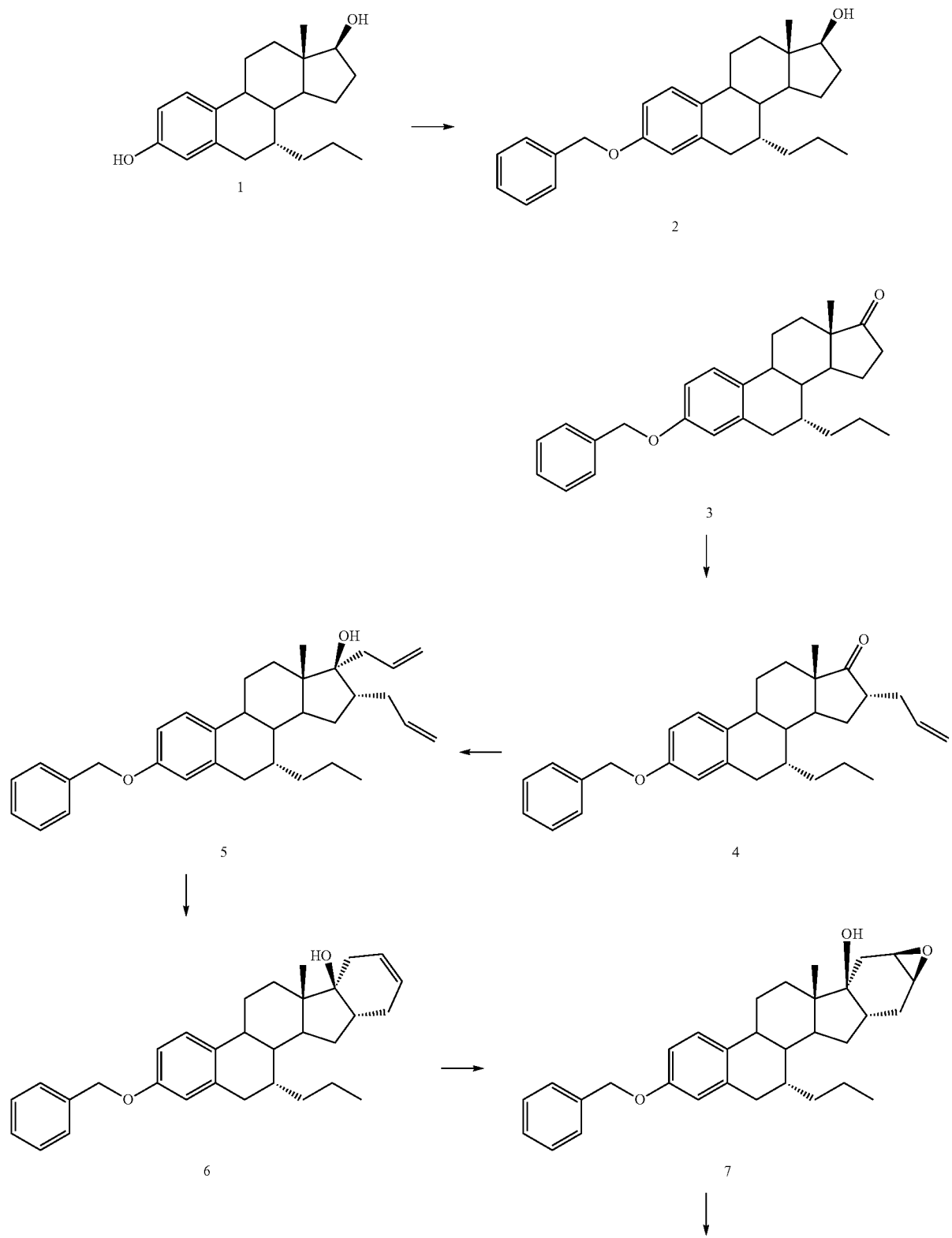

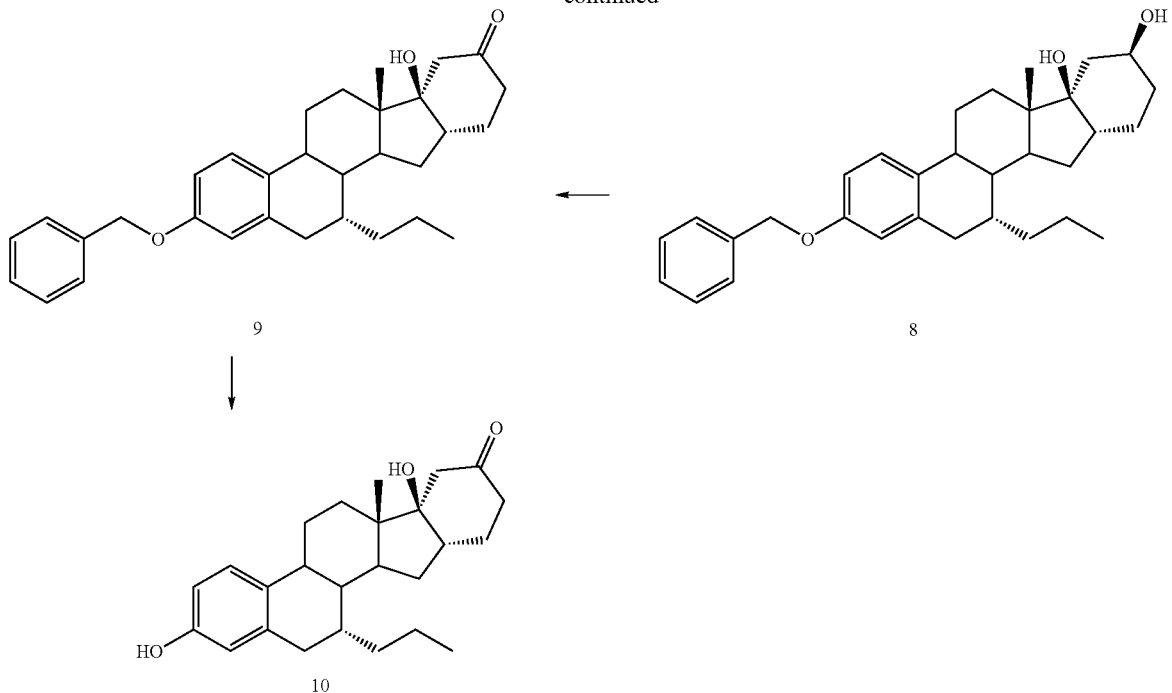

The synthesis of steroid derivatives in general has been amply documented in literature (e.g., reference 2). Specifically, efficient procedures have been published for the introduction of halogens in the aromatic ring at position C1 or C4 (references 3 a-1).

To introduce fluorine, typically strong fluorinating reagents like N-fluoropyridinium triflate or N-fluorobis(trifluoromethyl)sulfonylimide can be used. The 2-F and 4-F isomers which generally result can be chromatographically separated. These operations are preferentially carried out at very early stages of the synthesis. More regioselective approaches comprise e.g. reaction of appropriate 4-ene-3-ones to the enamine, followed by reaction with perchloryl fluoride and subsequent aromatization to give 4-fluoroestradiols directly.

Another approach to selectively introduce fluorine consists of applying Schiemann-type reactions, by first isolating the 2- and 4-nitro derivatives, reducing them to the appropriate anilines and applying typical diazonium chemistry ($NaNO_2$—$HBF_4$).

Chlorination may be carried out with chlorinating reagents like sulfuryl chloride, leading predominantly to 4-chloroestrones or 4-chloroestradiol, whereas for selectively obtaining 2-chloro derivatives a more circuitous route is available, which starts from the 4-nitro derivative. This can be first chlorinated at the C2 position, after which a two-step reductive removal of the nitro group is accomplished; i.e. reduction to the aniline, conversion to a diazonium salt and removal with hypophosphoric acid.

An alternative direct method for regioselective introduction of chloro- or bromo-atoms entails conversion of 2-thallium(III)-complexes of estrones with copper chloride or copper bromide.

Alternative methods for synthesis of regio-isomers consist of dibromination to 2,4-dibromoestradiols, followed by regioselective reduction with either palladium on charcoal or the application of agents like KI, formic acid or ascorbic acid.

Introduction of alkyl substituents at the C7α-position is generally accomplished by reaction of 4,6-dien-3-ones with organocuprates, to produce 7α-alkyl-4-ene-3-ones, which upon aromatization provide 7α-alkylestra-1,3,5(10)-trien-3-ols. The 7β-isomers arising from these procedures (in variable amounts, depending on conditions and substituents) are removed either by chromatography or crystallization at appropriate stages (references 1, 7).

The C15β substituents are introduced stereoselectively by reaction of 15-ene-17-ones with organocuprates. In order to obtain the required 15α-isomers, a double bond is introduced again (e.g. by Saegusa oxidation of 17-silylenolates), which upon catalytic reduction forces the C15 substituent in a 15α position (reference 4). Alternatively, 15α-substituted estrones are obtained by initial introduction of a 15β cyano group, which upon base-catalysed isomerization is converted into a 15α-cyano group and as such suitable for functional group interconversion to the desired 15α-derivatives (reference 5). A direct approach to synthesize 15α-alkyl steroids consists of biomimetic total synthesis as exemplified with the construction of 15α-methyl estrone.

In the case that 13-ethyl derivatives are required, 13-ethylestrone or 13-ethylnordion, both available via total synthetic methods (as amply documented in the chemistry of contraceptive steroids), may be used as starting materials in the sequences outlined in Schemes 1 and 2.

A compound according to the invention can be used in therapy by direct administration of the pharmaceutically purified compound without additives, but it is more common and more convenient to manufacture a pharmaceutical formulation of the compound with one or more pharmaceutical excipients and/or additives. Such formulations can be adapted for particular routes of administration, such as the oral, buccal, parenteral, transdermal, transmucosal and vaginal route. Each route of administration requires special adaptations in order to optimize the absorption into the systemic circulation of the recipient or to optimize local action in target tissue of the recipient.

Further routes of administration of the medicines comprising a compound according to the invention can be for injection into veins, subcutaneously or intra-muscularly. The compounds may also be administered with aids to obtain transdermal or transmucosal resorption into the body of the recipient. 'Transmucosal' means, for example, absorption within the oral cavity, within the nose, within the vagina or via rectal tissue. Suitable dosage forms for buccal, pulmonary or nasal administration can be prepared with sprays or suppositories. The recipient can be a human or an animal.

As the diseases in which the compounds can be used are in the area of women's health care the vaginal route of administration is also contemplated. A medicine can be formulated in the form of a device for vaginal drug delivery such as in admixture with a flexible polymer for a removable intrauterine device or a removable vaginal device, for example in the form of a ring. Polymers or other additives can also be used for a parenteral implant, such as a subcutaneous implant for extended release of a drug according to the invention. As such, extended release formulations or other formulations aimed at particular absorption profiles are also within the scope of the invention. A compound according to the invention, in particular compound 10, is very well soluble in water, in particular in comparison to Org 41621 (See WO2002/00682). This offers an advantage for uses in the manufacture of medicines wherein higher solubility is desirable, such as a drinkable or injectable formulation.

A compound according to the invention shall be administered to a recipient for the intended therapeutic purpose in a therapeutically effective amount. A therapeutic amount to be selected for a recipient may depend on recipient's weight, health condition, disease severity, side-effect risks and administration route. In general the daily dose or amount in a dosage unit for daily dosing will be within the range of from 1000 mg to 0.005 mg. A more preferred range is from 10 mg to 0.05 mg. For extended release formulations and devices the amount in the formulation is higher for release of the daily amount as indicated above.

Compounds according to the invention may also be used for diagnostic purposes. For example, isotope labeled compounds can be used to identify pathology or to trace the presence of molecules in particular locations in the body of a patient. The present invention also embraces isotopically-labelled compounds according to formula I. This formula and manner of defining the compounds according to the invention includes for example deuterated compounds, as is customary in this manner of representation of a group of compounds. Other examples of isotopes that can be incorporated into compounds of the invention include isotopes of hydrogen, carbon, halogens or oxygen, such as $^2H$, $^3H$, $^{13}C$, $^{14}C$, $^{18}O$, $^{35}S$, $^{18}F$, and $^{36}Cl$, respectively. Substitution with heavier isotopes such as deuterium (i.e. $^2H$) may afford certain therapeutic advantages resulting from greater metabolic stability (e.g., increased in vivo half-life or reduced dosage requirements) and hence may be preferred in some circumstances. $^{11}C$ and $^{18}F$ are the preferred isotopes to be incorporated in a compound of the invention for use as a PET (Positron Emission Tomography) tracer. Isotope-labelled compounds of Formula 1 can generally be prepared by following procedures analogous to those disclosed in the Schemes and/or in the Examples herein below, by substituting an appropriate isotope-labelled reagent for a non-isotope-labelled reagent.

EXAMPLES

Examples for Synthesis According to Scheme 2

(If by the naming of the compounds in this specification an ambiguity arises on the chemical structure of a compound and the ambiguity in the name cannot be clarified by correcting as an obvious error in view of the whole contents of this specification, the structures drawn in the schemes are decisive to determine the intended structure.)

(7α,17β-7-propylestra-1,3,5(10)-trien-3,17-diol (Compound 1)

To a solution of 360 mg of 7α,17β-7-propylestra-1,3,5 (10)-trien-3,17-diol-(17-acetate) (see ref 1) in a mixture of 10 ml of THF and 10 ml of methanol was added 150 mg of NaOH. The mixture was stirred for 2 hr at rt. Then the reaction was concentrated and the residue diluted with water and acidified with 1N HCl. The product was extracted with ethyl acetate. The extract was washed with water, dried and concentrated, and the residue was chromatographed over silica gel, using a gradient of heptane/ethyl acetate as eluent. The purified material thus isolated was treated with acetone water, to give 250 mg of white crystalline material; Mp 104-107° C.

$R_f$ 0.24 (heptane/ethyl acetate 7/3). NMR (CDCl$_3$) 0.77 (s, 3, CH$_3$), 0.87 (t, 3, CH$_3$), δ 2.76 and 2.85 (dd, 2, CH$_2$), 3.72 (t, 1, CHOH), 6.52 (d, 1, H-4), 6.62 (dd, 1, H-2), 7.12 (d, 1, H-1).

(7α,17β)-3-(phenylmethoxy)-7-propylestra-1,3,5 (10)-trien-17-ol (Compound 2)

To a solution of 5 gr of (7α,17β)-7-propylestra-1,3,5(10)-triene-3,17-diol in 15 ml of DMF was added 13 gr of K$_2$CO$_3$ and 3.3 ml of benzyl bromide.

The reaction was stirred for 3 hr and then worked up by pouring onto water, extraction with ethyl acetate, drying and concentration. The crude material was chromatographed over SiO$_2$, to provide 6.1 gr of (7α,17β)-3-(phenylmethoxy)-7-propylestra-1,3,5(10)-trien-17-ol.

Rf 0.32 (heptane/ethyl acetate 7/3).

NMR (CDCl$_3$): 0.77 (s, 3H, 18-CH$_3$), 0.87 (t, 3H, CH$_3$-prop.), 5.02 (s, 2H, CH$_2$O-benzyl), 3.76 (m, 1H, CHOH), 6.71 (d, 1H, H4), 6.78 (dd, 1H, H2), 7.20 (d, 1H, H1), 7.28-7.44 (m, 5H, benzylarom).

(7α)-3-(phenylmethoxy)-7-propylestra-1,3,5(10)-trien-17-one (Compound 3)

A solution of 30 g of 15% NaOCl in water and 0.15 g of NaBr were added at 0-5° C. to a solution of 10 g of (7α,17β)-3-(phenylmethoxy)-7-propylestra-1,3,5(10)-trien-17-ol and 200 mg of TEMPO in 80 ml of ethyl acetate. The mixture was vigorously stirred and the reaction monitored by tlc.

After completion of the reaction, excess reagent was destroyed by adding a solution of 15 g of Na$_2$S$_2$O$_3$ in 100 ml of water while cooling to 5-10° C. After stirring for ½ hr the organic layer was separated and the aqueous phase was extracted once with ethyl acetate. The combined organic layers were washed with water, dried and concentrated, and the product purified by chromatography over silica gel, to give 8.5 g of compound 3, $R_f$ 0.50 (heptane/ethyl acetate 7/3)

NMR (CDCl$_3$): 0.89 (t, 3H, CH$_3$), 0.90 (s, 3H, 18CH$_3$), 2.80 (d, 1H, 6CH$_2$), 2.93 (dd, 1H, 6CH$_2$), 5.02 (s, 2H, CH$_2$O—).

(7α,16α)-3-(phenylmethoxy)-16-(2-propenyl)-7-propylestra-1,3,5(10)-trien-17-one (Compound 4)

A solution of 10.3 ml of 1M LiHMDS was added to 15 ml of dry THF and cooled to −40° C. Subsequently, a solution of 4.65 g of (7α)-3-(phenylmethoxy)-7-propylestra-1,3,5(10)- trien-17-one in 15 ml of THF was added dropwise and stirring at −40° C. was continued for 1 hr. A solution of 1.05 ml of allyl bromide in 5 ml of THF was added dropwise, the mixture was stirred at −20° C. for an additional hr and then poured onto sat NH$_4$Cl and extracted with ethyl acetate. The organic layer was washed, dried and concentrated, and the product purified by chromatography, to provide 4.2 g of 4.

R$_f$ 0.65 (heptane/ethyl acetate 7/3)

NMR (CDCl$_3$): 0.89 (t, 3H, propyl CH$_3$), 0.94 (s, 3H, 18CH$_3$), 2.77 and 2.92 (d+dd, 2H, H6), 5.04 (s, 2H, CH$_2$OPhe), 5.09 (m, 2H, allylCH$_2$), 5.75 (m, 1H, allylCH).

(7α,16α,17β)-3-(phenylmethoxy)-7-propyl-16,17-bis(2-propenyl)estra-1,3,5(10)-trien-17-ol (Compound 5)

To a solution of 29.2 ml of 1M allylmagnesium bromide in ether was added 80 ml of dry THF. The mixture was cooled to −60° C. and a solution of 10 g of (7α,16α)-3-(phenylmethoxy)-16-(2-propenyl)-7-propylestra-1,3,5(10)-trien-17-one in 50 ml of THF was added dropwise. The mixture was stirred for an additional ½ hr at −60° C. and allowed to rise to 0° C., and stirred at that temperature for 1 hr. The reaction mixture was poured into sat NH$_4$Cl and extracted with ethyl acetate. The organic layer was once washed with sat NaCl and dried and concentrated. The remainders were chromatographed over SiO$_2$ (heptane/ethyl acetate) to provide 7.2 g of Compound 5.

R$_f$ (heptane/ethyl acetate 9/1) 0.26 (starting material 0.45). NMR (CDCl$_3$): 0.89 (t, 3, propyl), 0.95 (s, 3H, 18-CH$_3$), 2.75-2.85 (d+dd, 2H, 6-CH$_2$), 5.02 (s, 2H, CH$_2$-benzyl), 4.98-5.20 (m, 4H, 2× allyl CH$_2$), 5.79 and 6.07 (2×m, 2H, allyl CH), 6.70 (d, 1H, H-4), 6.87 (dd, 1H, H2), 7.18 (d, 1H, H1), 7.30-7.44 (m, 5H, benzyl).

(7α,16β,17α)-3-(phenylmethoxy)-7-propyl-16,24-cyclo-19,21-dinorchola-1,3,5(10),22-tetraen-17β-ol (Compound 6)

To a solution of 6.7 g of Compound 5 in 120 ml of dichloromethane was added 0.4 g of Grubbs catalyst, and the mixture was stirred at RT. After 1 hr an additional portion of 0.4 g of catalyst was added and stirred for 1 additional hr to completion of the reaction.

The solvent was evaporated, and 150 ml of toluene and 40 g of Al$_2$O$_3$ were added. The mixture was stirred for 1 hr at 60° C. and then filtered over Celite. The filtrate was concentrated to give 6.17 g of the product.

NMR (CDCl$_3$): 0.87 (t, 3H, propyl), 0.98 (s, 3H, 18-CH$_3$), 2.74 and 2.90 (d+dd, 2H, 6-CH$_2$), 5.02 (s, 2H, CH$_2$-benzyl), 5.96 (m, 2H, olefin cyclohexene), 6.70 (d, 1H, H-4), 6.87 (dd, 1H, H2), 7.21 (d, 1H, H1), 7.16-7.44 (m, 5H, phenyl).

(7α,16β,17α,22β,23β)-22,23-epoxy-3-(phenylmethoxy)-7-propyl-16,24-cyclo-19,21-dinorchola-1,3,5(10)-trien-17-ol (Compound 7)

To a solution of 6 g of compound 6 in 150 ml of dichloromethane was added 6 g of NaHCO$_3$ and 3.9 g of 70% meta-chloroperbenzoic acid while keeping the reaction mixture at 0° C. The reaction was stirred at 0° C. for 2 hr. Water was added and the product was extracted with dichloromethane. The organic layer was washed once with 100 ml of 5% Na$_2$S$_2$O$_5$ solution, and dried and concentrated. The residue was chromatographed over silicagel (heptane/ethyl acetate gradient) to give 3.7 g of the β-epoxide 7.

R$_f$ 0.36 (tol/ethyl acetate) (R$_f$ of starting material 0.40. NMR (CDCl$_3$): 0.90 (s, 3H, CH$_3$O), 0.88 (t, 3H, CH$_3$), 2.55 (m, 1H, 9-H), 2.92 (dd, 1H, 6-CH$_2$), 2.75 (d, 1H, 6-CH$_2$), 3.32 (t, 1H, CHO-epoxide), 3.38 (t, 1H, —CHO— epoxide), 5.02 (s, 2H, CH$_2$O).

(7α,16β,17α,22β)-3-(phenylmethoxy)-7-propyl-16,24-cyclo-19,21-dinorchola-1,3,5(10)-triene-17,22-diol (Compound 8)

A solution of 4.16 g of epoxide 7 in 20 ml of dry THF was added dropwise to a suspension of 340 mg of LiAlH$_4$ in 30 ml of THF and then refluxed for 1 hr. The reaction was cooled to RT and the reagent quenched by subsequent addition of 0.35 ml of water, 0.35 ml of 18% NaOH, and 1.2 ml of water. The mixture was stirred for 10 min and then filtered over Celite and the filtrate was concentrated and the residue was purified by chromatography, to give 3.35 gr of compound 8;

Mp: 146-147° C.; R$_f$ 0.20 (tol./ethyl acetate 8/2).

NMR (CDCl$_3$): 0.88 (t, 3H, CH$_3$ propyl), 0.90 (s, 3H, 18-CH$_3$), 4.26 (br.m, 1H, CHOH), 5.02 (s, 2H, CH$_2$-benzyl), 6.70 (d, 1H, H4) 6.78 (dd, 1H, H2) 7.18 (d, 1H, H1), 7.15-7.44 (m, 5H, phenyl).

(7α,16β,17α)-17-hydroxy-3-(phenylmethoxy)-7-propyl-16,24-cyclo-19,21-dinorchola-1,3,5(10)-trien-22-one (Compound 9)

To a solution of 7.4 gr of N-methylmorpholine-N-oxide in 150 ml of dichloromethane was added 385 mg of tetrapropylammonium perruthenate and the mixture stirred for 5 min. Then 20 gr of compound 8 in 150 ml of dichloromethane was added. The reaction was complete after 4 hr. The mixture was concentrated to 100 ml and 150 ml of diethyl ether and 2 g of charcoal were added. Stirring was continued overnight. The solids were filtered over Celite, and the filtrate was concentrated, and the residue purified by passing through a short silica column, to provide 14.5 g of compound 9.

R$_f$ 0.25 (heptane/ethyl acetate 7/3)

NMR (CDCl$_3$): 0.88 (t, 3H, CH$_3$ propyl), 0.97 (s, 3H, 18-CH$_3$), 2.40 and 2.76 (dd, 2H, CHOH—CH$_2$—CO), 2.75 and 2.90 (dd, 2H, benzylic C6), 5.00 (s, 2H, CH$_2$O), 6.70 (d, 1H, H4), 6.79 (dd, 1H, H2), 7.19 (d, 1H, H1), 7.30-7.44 (m, 5H, phenyl).

(7α,16β,17α)-3,17-dihydroxy-7-propyl-16,24-cyclo-19,21-dinorchola-1,3,5(10)-trien-22-one (Compound 10)

A solution of 14 g of compound 9 in 280 ml of ethanol was charged with 1.4 g of 5% Pd/C and 1 ml of triethylamine. The mixture was hydrogenated under 1.5 atm. of H$_2$ gas. After completion of the reaction the hydrogen was pumped off, and replaced by nitrogen gas, and the mixture was filtered over Celite. The filtrate was concentrated and coevaporated several times to remove ethanol and then crystallized from 20 ml of ethyl acetate/toluene (1/1/v/v) to provide 8.05 of compound 10. R$_f$ (toluene/ethyl acetate 1/1) 0.45.

NMR (DMSO$^{d6}$): 0.82 (s, 3H, 18-CH$_3$), 0.86 (t, 3H, CH$_3$ propyl), 6.42 (d, 1H, H4), 6.50 (dd, 1H, H2), 7.05 (d, 1H, H1), 9.00 (s, 1H, 3-OH).

Compound 10 was purified by crystallisation from acetonitrile as follows:

The crude compound was dissolved in acetonitril and concentrated to 10 volume parts (1 g in 10 ml). Upon addition of a seed crystal crystallisation immediately occurred. After one night in the refrigerator the crystals were filtered off, washed with cold acetonitril and dried in vacuo at room temperature to constant weight. The crystals, obtained in 75% yield, contained 3.7% m/m acetonitril. The crystal form obtained in this manner is an acetonitril solvate of compound 10.

A purified crystalline ansolvate of compound 10 was obtained from the crystalline acetonitril solvate of compound 10 as follows:

The acetonitril solvate was transformed to an ansolvate by heating at 80° C. during 24 hr in vacuo.

Examples for Synthesis According to Scheme 1

(7α)-3-(phenylmethoxy)-7-propylestra-1,3,5(10)-trien-17-one dimethylhydrazone (Compound 11)

A solution of 35 g of (7α)-3-(phenylmethoxy)-7-propylestra-1,3,5(10)-trien-17-one in 150 ml of toluene was added 13 ml of dimethylhydrazine and 0.7 ml of TFA.

The reaction mixture was heated for 3 hr at 110° C. The reaction mixture was then cooled to RT and poured onto 100 ml of sat.NaHCO$_3$ solution. The organic layer was separated, washed once with satNaHCO$_3$ and dried and concentrated. The residue was chromatographed over SiO$_2$, to give 25 gr of the dimethylhydrazone.

$R_f$ 0.27 (heptane/ethyl acetate 7/3).

NMR (CDCl$_3$): 0.85-0.89 (tr+s, 6H, 18-CH$_3$+propyl-CH$_3$), 2.48 (s, 6H, dimethylhydrazone), 6.71 and 6.79 (d+dd, 2H, H2 and H4).

(7α,16α)-16-[2-(2-methyl-1,3-dioxolan-2-yl)ethyl]-3-(phenylmethoxy)-7-propylestra-1,3,5(10)-trien-17-one dimethylhydrazone (Compound 12)

To a solution of 8.2 g of compound 11 in 50 ml of dry THF was added dropwise 12.5 ml of a 1.6 M solution of BuLi in hexanes at −60° C. After stirring for 15 min at −60° C., the mixture was kept at 0° C. for 15 min and then cooled again to −60° C. Then 3.3 ml of DMPU was added, followed by dropwise addition of 6.6 g of 2-(2-iodoethyl)-2-methyl-1,3-dioxolane in 10 ml of THF. The reaction was stirred for 2 hr at −60° C. and then quenched by addition of 300 ml of 10% NH$_4$Cl, and extracted twice with ethyl acetate. The organic layer was once washed with water, dried and concentrated. The remainders were chromatographed over silicagel, to give 5.2 g of compound 12. NMR (CDCl$_3$): 0.87 (s, 3H, 18CH$_3$), 0.89 (t, 3H, CH$_3$propyl), 1.34 (s, 3H, CH$_3$-dioxolane), 2.42 (s, 6H, N-dimethyl), 3.95 (m, 4H, dioxolane CH$_2$), 5.2 (s, 2H, OCH$_2$-phenyl).

$R_f$ 0.41 (heptane/ethyl acetate 6/4).

(7α,16α)-16-(3-oxobutyl)-3-(phenylmethoxy)-7-propylestra-1,3,5(10)-trien-17-one (Compound 13)

A solution of 5.0 g of oxone in 15 ml of water was added dropwise to a solution of 2.27 g of compound 12 in 5 ml of acetone. The reaction was stirred overnight at room temperature and then diluted with water and the product extracted into ethyl acetate. The organic layer was once washed with water, dried and concentrated. The remainders were chromatographed over silicagel to provide 1.3 g of compound 13

$R_f$ 0.50 (heptane/acetone 6/4).

NMR (CDCl$_3$): 0.90 (t, 3H, CH$_3$propyl), 0.93 (s, 3H, 18CH$_3$), 2.18 (s, 3H, CH$_3$CO) 2.79, 2.93 (d, and dd, 2H, 6CH$_2$), 5.02 (s, 2H, CH$_2$O), 6.72 (d, 1H, H4), 6.80 (dd, 1H, H2), 7.20 (d, 1H, H1)

(7α,16β,17α)-17-hydroxy-3-(phenylmethoxy)-7-propyl-16,24-cyclo-19,21-dinorchola-1,3,5(10)-trien-22-one (Compound 9)

A solution of lithiumhexamethyl disilazide was prepared by adding 4.8 ml of 1.6 m BuLi in hexanes to a solution of 1.8 ml of hexamethyldisilazane in 10 ml of dry THF at −40° C. This solution was stirred for 15 min at −40° C. A quantity of 7.8 ml of this solution was added dropwise to a solution of 1.34 g of compound 13 in 20 ml of dry THF at −70° C. The mixture subsequently stirred at −70° C. for an additional hr and then poured into 50 ml of sat. NH$_4$Cl solution and extracted with ethyl acetate.

The organic layer was washed, dried and concentrated and purified by chromatography, to provide 0.76 g of compound 9. $R_f$(heptane/ethyl acetate 7/3) 0.25 (for starting material $R_f$ 0.50). NMR (DMSO$^{d6}$): 0.82 (s, 3H, 18-CH$_3$), 0.86 (t, 3H, CH$_3$ propyl), 6.42 (d, 1H, H4) 6.50 (dd, 1H, H2) 7.05 (d, 1H, H1), 9.00 (s, 1H, 3-OH).

Examples of Biological Effects

Pharmacological In Vitro Profile (7α,16β,17α)-3,17-dihydroxy-7-propyl-16,24-cyclo-19,21-dinorchola-1,3,5(10)-trien-22-one (Compound 10) is unique in having a combined partial ER/partial PR (ant)agonistic profile with an EC50 of 1.8 nmol/L for ERα and of 3.8 nmol/L for progesterone receptor B (PR-B). (7α,16β,17α)-3,17-dihydroxy-7-propyl-16,24-cyclo-19,21-dinorchola-1,3,5(10)-trien-22-one is an antagonist for the androgen receptor (AR) with an IC50 of 125 nM.

Pharmacology data for (7α,16β,17α)-3,17-dihydroxy-7-propyl-16,24-cyclo-19,21-dinorchola-1,3,5(10)-trien-22-one in comparison to the known hydroxyl analogue, (7α,16β,17α,22β)-7-propyl-16,24-cyclo-19,21-dinorchola-1,3,5(10)-triene-3,17,22-triol (Org 41621; WO2002/00682) are summarized in Table 1.

TABLE 1

| In vitro nuclear receptor profile for Compound 10 | | |
|---|---|---|
| Assay | Compound 10 | Org 41621 |
| Vitro data | | |
| ERα ago EC50; eff | 1.8 nM; 0.63 | 0.28 nM; 0.95 |
| ERα ant IC50; anteff | 10.0 nM; 0.47 | >1,000 nM |
| ERβ ago EC50; eff | >10,000 nM | >100 nM |
| ERβ ant IC50; anteff | 8.4 nM; 0.83 | 3.8 nM; 0.89 |
| PR-B ago EC50; eff | 3.8 nM; 0.49 | >100 nM |
| PR-B ant IC50; anteff | 3.7 nM; 0.55 | 20.8 nM; 0.74 |
| PR-A ago EC50; eff | 30.0 nM; 0.46 | >100 nM |
| PR-A ant IC50; anteff | 27.0 nM; 0.54 | 58.3 nM; 0.85 |

From the vitro nuclear receptor data it can be concluded that compound 10 is a partial (ant)agonist for PR-B and PR-A with nanomolar activity. Besides its activity at PR, Compound 10 shows partial (ant)agonist activity at ERα in the low nanomolar range and is a full antagonist at ERβ.

In Vivo Data

In a 4-week phase I study, female human volunteers were exposed to the compound (7α,16β,17α)-3,17-dihydroxy-7-propyl-16,24-cyclo-19,21-dinorchola-1,3,5(10)-trien-22-one (Compound 10) at blood plasma level with Cmax of 16 nM, endometrial biopsies were obtained on day 29. Exposure to compound 10 was effectuated by administration of an oral dosage of 10 mg daily of Org 41621 which gives rise to compound 10 by metabolism. Histopathology scores showed mostly atrophic or inactive endometrium with some subjects showing conversion to secretory (P-type) endometrium. There were no signs of hyperplasia.

In intact, regularly cycling, female monkeys Compound 10 was shown to inhibit ovulation in two different species (*Macaca arctoides* and *Macaca fascicularis*) upon 21 days once-a-day oral dosing. The minimal active dose (MAD) for ovulation inhibition upon oral dosing in gelatine/mannitol was established at <=0.1 mg/kg per day.

In view of the in vitro pharmacological profile, the observed endometrial tissue response in postmenopausal women and the demonstrated capacity to inhibit ovulation in non-human primates, represents that compound 10 effectively reduces estrogenic stimulation of both endometrial and endometriotic tissue next to inducing a state of amenorrhea. The present pharmacodynamic profile represents therapeutic efficacy in the treatment of endometriosis.

In intact, regularly cycling, female rats Compound 10 was shown to inhibit ovulation with a minimal active dose (MAD) of 0.1 mg/kg per day. In line with this, it was demonstrated that Compound 10 was able to effectively suppress circulating levels of LH and FSH in ovariectomized female rats in a 4-week multiple dose study both after oral and subcutaneous application in gelatine/mannitol. In the same series of studies it was demonstrated that Compound 10 behaves as an estrogen receptor agonist on vaginal tissue, cholesterol metabolism and bone, the latter as measured by support of bone mineral density and a reduction of circulating osteocalcin. Besides efficacy on the regulation of LH/FSH, activation of estrogen receptors in the CNS was demonstrated by showing a near full agonist response to Compound 10 in the lordosis model (facilitation of female sexual behaviour). Unlike non-selective full agonist estrogens such as 17β-estradiol (E2) and ethynyl-estradiol (EE), Compound 10 only mildly stimulates rat uterine tissue (FIG. 1). Summary data for in vivo studies in the rat are summarized in Table 2.

TABLE 2

| In vivo data obtained in rat for Compound 10 and Ethynyl-Estradiol (EE) | | |
|---|---|---|
| Assay | EE | Compound 10 |
| In Vivo data | | |
| Allen-Doisy (rat) MAD p.o. | 0.016 mg/kg · day | 0.15 mg/kg · day |
| AOST BMD (rat) MAD p.o. | 0.020 mg/kg · day | 0.12 mg/kg · day |
| Lordosis (rat) MAD p.o. | 0.035 mg/kg · day | 0.14 mg/kg · day |
| Ovulation Inhibition (rat) MAD p.o. | 0.022 mg/kg · day | 0.10 mg/kg · day |

Embryofetal Safety

Embryofetal safety was observed in embryofetal toxicity studies in rats, wherein a compound according to the invention has demonstrated lack of teratogenic activity.

Oral gavage administration of Org 41621 to pregnant rats during the organogenesis phase of gestation at 0.03, 0.09 and 0.15 mg/kg/day resulted in maternal bodyweight loss or low weight gain and reduced food intake. Treatment at 0.09 and 0.15 mg/kg was associated with a clear increase in the mean number of early resorptions per litter (with post implantation loss of 15 and 24%, respectively) and an increase in major fetal abnormalities principally affecting the ribs, humerus and scapula (3/273 fetuses and 11/216 fetuses, respectively).

Oral gavage administration of Compound 10 to pregnant rats during the organogenesis phase of gestation at doses of 0.03, 0.1, 0.3, 0.5, 1, 3 and 10 mg/kg/day caused in the dams at 0.1 mg/kg/day up to and including 10 mg/kg/day, a significant reduction in body weight gain. Compound 10 induced early resorptions at dosages >0.3 mg/kg (with post implantation loss of approx. 80%). No major defects were observed in the Org 44920 treated groups, except for a few minor defects at 0.1 mg/kg (wavy ribs with an incidence of 4/153 fetuses). No effects were observed at 0.3 mg/kg (based on a total of 13 fetuses).

In conclusion, based on the results of the preliminary embryofetal development study in the rat with compound 10, up to a dose of 0.3 mg/kg, showed no evidence of teratogenicity in the rat (although the number of fetuses and litters is still limited).

REFERENCES

1a) Bulun et al., N Engl J Med 2009; 360:268-79

1b) H. J. J. Loozen et al, EPO 869 132 A1

2) See e.g. J. Fried and J. Edwards, Organic Reactions in Steroid Chemistry, Vol I/II; Nostrand Reinhold Company, New York, 1972; and C. Djerassi, Steroid Reactions; Holden-Day Inc., San Francisco 1960

3a) A. J. Tomson, J. P. Horwitz, J. Org. Chem., 24, 2056 (1959)

3b) W. T. Pennington, G. Resnati, D. D. Dessmarteau, J. Org. Chem., 57, 1536 (1992)

3c) T. Utne, R. B. Jobson, R. B. Babson, J. Org. Chem., 33, 2469 (1969)

3d) H. Ali, J. Rousseau, T. G. Gantchev, J. E. van Lier, J. Med. Chem., 36, 4255 (1993)

3e) H. Ali, J. Rousseau, J. E. van Lier, J. Med. Chem., 36, 3061 (1993)

3f) V. C. O, Njar, T. Arunachalam, E. Caspi, J. Org. Chem., 48, 1007 (1983)

3g) Y. Seimbille, H. Ali, J. van Lier, J. Chem. Soc., Perkin Trans 1, 657 (2002)

3h) P. C. Bulman Page, F. Hussain, J. Maggs, P. Morgan, B. K. Park, Tetrahedron, 46, 2059 (1990)

3i) D. S. Wilbur, H. A. O'Brien Jr., J. Org. Chem., 47 (2), 359 (1982)

3j) E. Schwenk, C. G. Castle, E. Joachim, J. Org. Chem., 28, 136 (1963)

3k) P. C. Bullman Page, F. Hussain, N. M. Bonham, P. Morgan, J. L. Maggs, B. Kevin Park, Tetrahedron, 47, 2871 (1991)

3l) M. Numazawa, K. Kimura, M. Ogata, M. Nagaoka, J. Org Chem, 50 (25), 5421 (1985)

4) J. R. Bull, M. Loedolff, J. CHem. Soc., Perkin Trans. I, 1269 (1996)

5) M. B Groen, F. J. Zeelen, Rec. Tray. Chim. Pays Bas 98 (4), 239 (1979)

6a) E. Keinan, S. C. Sinha, A. Sinha-Baghi, J. Chem. Soc., Perkin Trans 1, 3333 (1991)

6b) Q. Zhang, Y. Wu, Tetrahedron, 63, 10407 (2007).

6c) B. M. Trost, R. A. Kunz, J. Amer. Chem. Soc., 97, 7152 (1975).

7) H. J. J. Loozen, A. G. H. Ederveen, F. A. Dijcks, WO 2006/027347 A1.

What is claimed is:

1. A compound of the formula

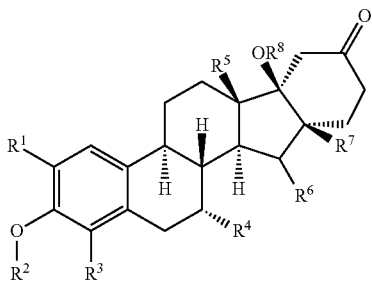

wherein
- $R^1$ is H or halogen;
- $R^2$ is H, (1C-4C)alkyl, (1C-4C)acyl, glucuronyl or sulfamoyl;
- $R^3$ is H or halogen;
- $R^4$ is H, (1C-4C)alkyl, (2C-4C)alkenyl or (2C-4C)alkynyl;
- $R^5$ is methyl or ethyl;
- $R^6$ is H or methyl;
- $R^7$ is H or methyl;
- $R^8$ is H or acyl.

2. The compound according to claim 1, wherein $R^8$ is H.

3. The compound according to claim 1 or 2, wherein $R^1$ is H or F and $R^3$ is H or F.

4. The compound according to claim 1 or 2, wherein $R^6$ is H or α-methyl.

5. The compound according to claim 1 or 2, wherein $R^5$ is methyl.

6. The compound according to claim 1 or 2, wherein $R^4$ is (1C-4C)alkyl.

7. The compound according to claim 6, wherein $R^4$ is propyl.

8. The compound according to claim 5, wherein $R^6$ is H and $R^7$ is H.

9. The compound according to claim 3, wherein $R^5$ is methyl; $R^6$ is H and $R^7$ is H.

10. The compound according to claim 9, wherein $R^4$ is propyl.

11. The compound according to claim 1, wherein $R^2$ is H or (1C-4C) acyl.

12. The compound according to claim 11, wherein $R^1$ is H; $R^3$ is H; $R^4$ is propyl; $R^5$ is methyl; $R^6$ is H and $R^7$ is H.

13. A compound of the formula

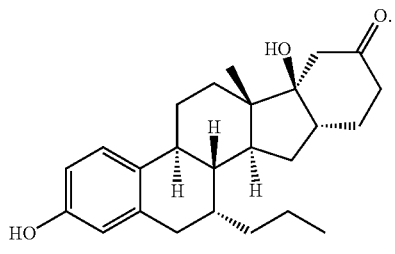

14. A pharmaceutical composition comprising a compound according to claim 1 and one Or more pharmaceutical excipients.

15. A pharmaceutical composition comprising the compound according to claim 13 and one or more pharmaceutical excipients.

16. A method of treatment for endometriosis comprising administering a compound of the formula

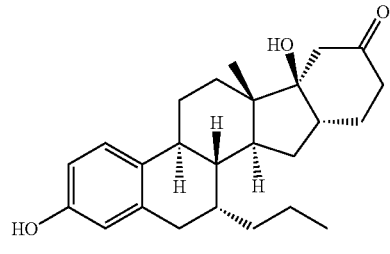

in a pharmaceutical formulation at a therapeutically effective dose.

17. A method of contraception comprising administration to a woman of a compound according to claim 1.

18. A method of treatment for endometriosis in a woman by administration of the compound according to claim 1 in a pharmaceutical formulation at a therapeutically effective dose.

* * * * *